United States Patent
Wellstood et al.

(10) Patent No.: US 6,571,183 B1
(45) Date of Patent: May 27, 2003

(54) IMAGING USING SPATIAL FREQUENCY FILTERING AND MASKING

(75) Inventors: Frederick Charles Wellstood, Lanham, MD (US); Sojiphong Chatraphorn, College Park, MD (US); Erin Franklin Fleet, Greenbelt, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/647,940

(22) PCT Filed: Jul. 8, 1999

(86) PCT No.: PCT/US99/12372

§ 371 (c)(1),
(2), (4) Date: Oct. 18, 2000

(87) PCT Pub. No.: WO00/20879

PCT Pub. Date: Apr. 13, 2000

Related U.S. Application Data

(60) Provisional application No. 60/103,058, filed on Oct. 5, 1998.

(51) Int. Cl.$^7$ .............................................. G01R 25/00
(52) U.S. Cl. .................... 702/65; 702/117; 702/193; 324/301; 324/313; 324/377; 382/147; 382/145; 382/312
(58) Field of Search ............................. 702/57, 64–67, 702/75–77, 117–118, 120–124, 126, 159, 172, 183, 189, 193, 197, 190, FOR 103, 104, 106, 110, 131, 134, 135, 164; 382/100, 147, 145, 312, 320, 280, 276, 285, 286, 287; 356/237.1, 237.2, 237.3, 433; 324/300, 301, 313, 376, 377, 200, 213, 219; 250/255, 559.01, 559.04, 559.06, 208.3

(56) References Cited

U.S. PATENT DOCUMENTS

| | | | |
|---|---|---|---|
| 5,451,863 A | 9/1995 | Freeman | |
| 5,491,411 A | 2/1996 | Wellstood et al. | |
| 5,726,571 A | * 3/1998 | Guclu et al. | ................. 324/322 |
| 5,834,938 A | 11/1998 | Odawara et al. | |
| 5,894,220 A | 4/1999 | Wellstood et al. | |

OTHER PUBLICATIONS

Pesikan et al., Two–Dimensional Current Density Imaging, Dec. 1990, IEEE, vol. 39, No. 6, pp. 1048–1053.*
Edminister, Theory and Problems of Electromagnetics, Jan. 1993, McGraw–Hill Inc, 2$^{nd}$ Edition, pp 76, 117 and 208.*

* cited by examiner

Primary Examiner—Marc S. Hoff
Assistant Examiner—Elias Desta
(74) Attorney, Agent, or Firm—Squire, Sanders & Dempsey LLP

(57) ABSTRACT

A method of, an and apparatus for, creating an image of currents flowing through current paths in a microelectronic circuit such that the image of the currents has improved spatial resolution using filters. The filters increase the spatial resolution and eliminate noise and edge artifacts in magnetic field and electric field images of electronic circuits. In accordance with the method, a magnetic field image is created with a scanning SQUID microscope. A magnetic inversion technique is then used to convert the magnetic field image into a current density image. The current density image is filtered based upon known restrictions on the wiring geometry of the microelectronic circuit being imaged. The technique can also be applied to convert electric fields of a circuit from a scanning single electron transistor microscope into images of the voltage levels on the wires in the circuit.

41 Claims, 12 Drawing Sheets

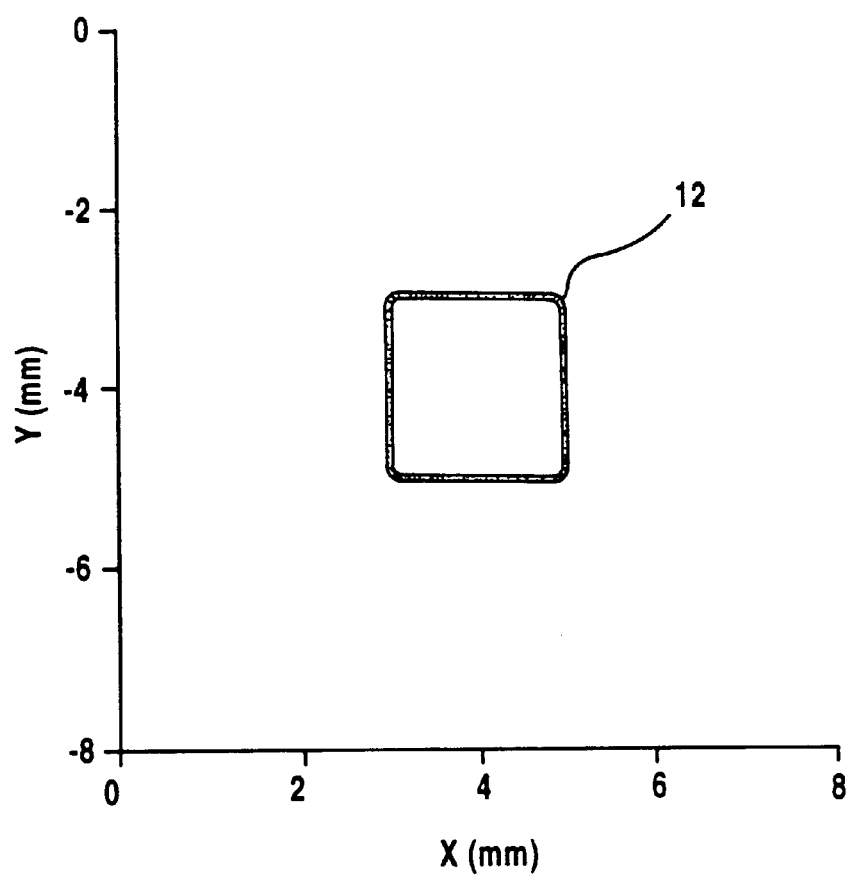

IMAGING USING SPATIAL FREQUENCY FILTERING AND MASKING

CROSS REFERENCE TO RELATED APPLICATIONS

This application is based upon United States Provisional Patent Application Serial No. 60/103,058, filed on Oct. 5, 1998. The contents of this provisional application are hereby incorporated by reference.

BACKGROUND OF THE INVENTION

1. Field of the Invention

The present invention is directed toward a filtering and masking technique for use with an output of a magnetic scanning device such as a scanning SQUID microscope. In particular, the invention is directed toward filtering and masking for converting magnetic field images into images of current density, converting magnetic field images into images of magnetic charge density, and converting magnetic field images into images of magnetization. Additionally, the filters of the present invention can be applied to converting electric field images into electric charge density, converting electric field images into images of voltage, and converting electric field images into images of polarization. The invention is useful for such purposes as obtaining an image of currents flowing in a microelectronic circuit, imaging of magnetic media such as computer disk drives, films of magnetic materials, and also for imaging of other integrated circuit applications. In particular, the invention is directed toward a method of using restrictions placed upon circuit geometry to improve the spatial resolution of an image of currents flowing in an electronic circuit. The present invention can also be used with the output of an electric field scanning device such as a scanning SET (Single Electron Transistor) microscope to obtain an image of the voltage level on wires or electrical components in the circuit.

2. Description of the Related Art

A number of techniques have been developed to image magnetic fields at length scales of a few $\mu m$ or smaller. These include decoration techniques, magnetoresistive or Hall probe sensors, flux-gate magnetometers, magneto-optic thin films, magnetic force microscopy, and electron beam interferometry. In particular, it has been determined that a magnetic flux microscope using a thin-film Superconducting Quantum Interference Device (SQUID) as a scanning device, such as that disclosed in U.S. Pat. No. 5,491,411, which is hereby incorporated by reference, can be used to obtain a magnetic image with a sufficiently high spatial and field resolution. Another example of a suitable scanning device is disclosed in U.S. Pat. No. 5,894,220, which is also incorporated by reference.

In the field of semiconductor/microelectronics testing, there is a need to measure the current flow and image the related current paths in semiconductor circuits and microelectronic devices. The devices currently used have proved to be of limited use in these endeavors because the images created are unclear due to noise, and allow for limited spatial resolution. Therefore, they cannot effectively image the flow of small currents in microelectronic structures.

It has also been determined that an SET microscope can be used as a scanning device, for scanning electric fields and imaging voltage levels on wires, rather than magnetic fields and imaging currents in wires using a scanning SQUID.

SUMMARY OF THE INVENTION

With the above discussed limitations of the prior art in mind, it is an object of the present invention to provide a spatial frequency filtering and masking technique, hereinafter referred to as spatial filtering and masking, or simply "filtering and masking", that can be used in conjunction with an output of a magnetic scanning device such as a scanning SQUID microscope to convert images of magnetic fields into images of current paths or wires in the microelectronic circuits. Such images enable identification of circuit faults, as well as identifying circuit structures without physically dismantling the circuit or the device containing the circuit. In particular, it is an object of the present invention to use novel signal processing filters to increase the signal-to-noise ratio of images of current flow or wires in microelectronic circuits.

It is also an object of the present invention to increase the spatial resolution obtainable from magnetic field images of microelectronic circuits when the images are mathematically transformed into images of current density flowing in a circuit.

It is yet another object of the invention to improve magnetic imaging techniques, so as to better enable them to locate the position of short circuits in microelectronic circuits.

In accordance with the above discussed objects, the present invention provides a spatial filtering and masking technique that cleans up background noise in Fourier space, and eliminates the edge effect from a finite sized data set. Without the spatial filtering and masking technique of the present invention, it is very difficult to obtain a high resolution picture of current paths because the background noise is exponentially amplified. In other words, the signal to noise ratio is small without the spatial filtering and masking technique. The spatial filtering and masking technique of the present invention can be used together with a scanning SQUID microscope, or other magnetic scanning device to convert magnetic fields into images of current paths or wires in the microelectronic circuits so that faults (if they exist) can be located. The filtering and masking technique can be incorporated into software which operates on a general purpose or special purpose computer, and which performs a Fourier transform of a magnetic field and converts the data into current paths.

Another object of the present invention is to provide a spatial frequency filtering and masking technique that can be used in conjunction with an output of an electric field scanning device such as a scanning SET microscope to convert electric fields into images of voltages on wires in microelectronic circuits. Such images enable identification of circuit faults, as well as identifying circuit structures without physically dismantling the circuit or the device containing the circuit. In particular, the present invention utilizes novel signal processing filters to increase the signal-to-noise ratio of images of voltage level on wires in microelectronic circuits.

It is also an object of the present invention to increase the spatial resolution obtainable from electric field images of microelectronic circuits when the images are mathematically transformed into images of voltage levels in a circuit.

BRIEF DESCRIPTION OF THE DRAWINGS

The present invention will be better understood by reference to the drawings, wherein:

FIG. 4 is an image of $J_x^2(x, y) + J_y^2(x, y)$ obtained from inverse Fourier transforms of the filtered data in FIGS. 3(a) and 3(b);

DETAILED DESCRIPTION OF THE PREFERRED EMBODIMENTS

Figure 1:
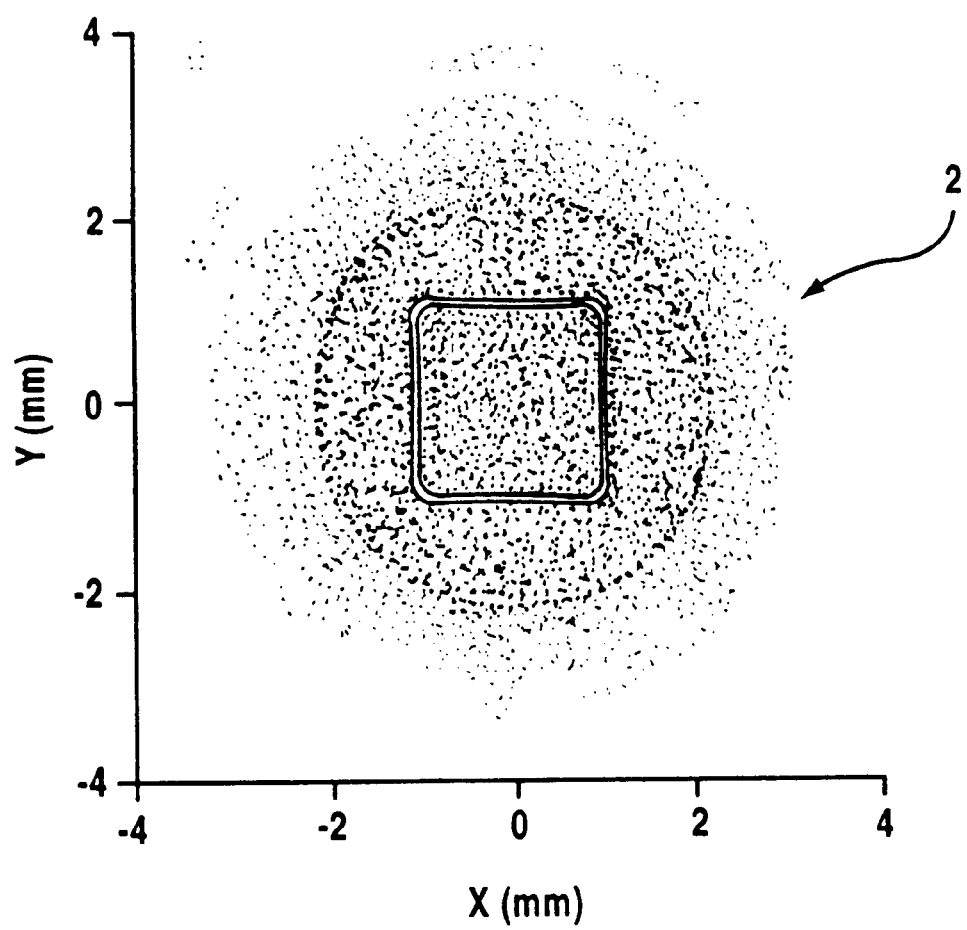
FIG. 1 is a graphic representation of a simulation of the normal component of the magnetic field generated by 100 $\mu A$ current flowing in a square loop of wire at a distance of 200 microns above the plane containing the loop.

The present invention is directed toward a novel apparatus for, and method of, imaging electronic circuits by using signal processing filters to process images of electric or magnetic fields from the circuits. In one embodiment, the input signal to the signal processing filters is a magnetic field image of a microelectronic circuit which is obtained using a scanning SQUID microscope. The SQUID microscope provides data comprised of voltage values corresponding to x-y positions on a scanned sample. The voltage values output from the SQUID electronics are directly proportional to the normal component of magnetic field in the SQUID generated by the sample. By orienting the SQUID loop so that it is facing perpendicular to the surface of the sample, rather than parallel to the surface of the sample, tangential components of the magnetic field can be detected by the SQUID. These voltage values can be plotted to obtain a false color image or gray scale image. Following an approach developed by John Wikswo at Vanderbilt University and others, referred to as back-evolution and as described below, such an image can be mathematically transformed into a picture of the currents flowing in the circuit thus allowing for the detection of short circuits and wiring faults. The filtering of the present invention is applied to the magnetic field data in order to remove noise from and de-blur the final images of the flowing currents in the microelectronic circuit obtained from the magnetic field data. Removing noise from the magnetic field data improves the spatial resolution of the image of the microelectronic circuit.

A preferred method of creating an image of currents flowing through a circuit in accordance with the present invention commences with the obtaining of magnetic field data corresponding to the normal component of magnetic fields above the circuit created by currents flowing in the circuit. Preferably, the magnetic field data is obtained through the use of a scanning SQUID microscope or a magnetic scanning device that detects magnetic fields generated by the currents flowing in devices such as integrated circuits and multi-chip modules. From knowledge of the magnetic field above a circuit, one can, in principle, infer where the currents are flowing in the circuit, thus allowing for the detection and diagnosis of circuit faults. However, magnetic field images are usually difficult to interpret directly in terms of the currents flowing in a sample, especially when there are many closely packed wires or a complicated wiring pattern. Therefore, in order to reliably find wiring faults in integrated circuits using magnetic field data, it is beneficial to convert images of magnetic field data into images of current paths. This is done using an established mathematical technique which is called "back-evolution" or also called "the magnetic inversion technique", as has been explained by Wikswo and others for example, in Instrumentation and Techniques for High Resolution Magnetic Imaging, by John P. Wikswo, Jr., Jan Van Egeraat, Yu Pei Ma, Nestor G. Sepulveda, Daniel J. Staton, Shaofen Tan, and Ranjith S. Wigesinghe, Digital Image Synthesis and Inverse Optics, SPIE Proceedings, Vol. 1351, pages 438–471, 1990. A number of software packages are available which allow a user to perform the complex mathematical functions necessary to perform a magnetic inversion technique and plot the results. An example of such software is TRANSFORM(™) by Fortner Research LLC.

The magnetic inversion technique is based on the Biot-Savart law, which relates current density to magnetic field strength. The main technique used in magnetic inversion is the application of a Fourier transform and spatial filtering to the measured magnetic field. In this technique, it is assumed that the current paths are confined to a sheet of thickness d which is much smaller than the SQUID-sample separation z. If this is not true the solution of the inversion technique is not unique. Typically, a SQUID is sensitive to only one component of magnetic field. For example, in one type of SQUID microscope the SQUID loop is oriented so as to lie in a plane which is parallel to the sample plane, which is called the X-Y plane, so that only the normal component $B_z$ is available.

$$B_z(x, y) \approx \frac{\mu_0 d}{4\pi} \int \int \frac{J_x(x', y') \cdot (y - y') - J_y(x', y') \cdot (x - x')}{[(x - x')^2 + (y - y')^2 + z^2]^{3/2}} dx' dy' \quad (1)$$

where $B_z(x, y)$ is the Z-component, also called the normal component, of the magnetic field at the point (x, y, z), $\mu_0$ is the permeability of free space, and $J_x$ and $J_y$ are the x and y components of current density, respectively, at position (x', y') in the sample. In equation (1), $B_z$ is a convolution of current density $J_x$ and $J_y$ with weighting functions. The convolution theorem allows us to write equation (1) in Fourier space as equation (2):

$$b_z(k_x, k_y, z) = \frac{i\mu_0 d e^{-kz}}{2k} [k_y \cdot j_x(k_x, k_y) - k_x \cdot j_y(k_x, k_y)] \quad (2)$$

where $b_z(k_x, k_y, z)$, $j_x(k_x, k_y)$ and $j_y(k_x, k_y)$ are the two dimensional Fourier transforms of the magnetic field and the current density, respectively, where i is the square root of −1. The $k_x$ and $k_y$ are the components of the spatial frequency $\bar{k}$. In equation (2), $j_x(k_x, k_y)$ and $j_y(k_x, k_y)$ are unknowns. However, using conservation of current we can obtain an additional equation which allows us to write $j_x(k_x, k_y)$ and $j_y(k_x, k_y)$ in terms of $b_z(k_x, k_y, z)$ in equations (3) and (4):

$$j_x(k_x, k_y, z) = \frac{i2}{\mu_0 d} e^{kz} \frac{k_y}{k} b_z(k_x, k_y, z) \quad (3)$$

$$j_y(k_x, k_y, z) = \frac{i2}{\mu_0 d} e^{kz} \frac{k_x}{k} b_z(k_x, k_y, z) \quad (4)$$

Here $k=\sqrt{k^2_x+k^2_y}$ is the magnitude of the spatial frequency vector $\bar{k}=(k_x, K_y)$. It should be noted that equations (3) and (4) blow up exponentially as k increases. In practice, the measured magnetic field data from the SQUID) consists of noise and a real signal from the current paths. The noise in the raw magnetic field data is Fourier transformed into the whole Fourier space and the noise is considerably amplified by the exponential terms at large values of k. Consequently the signal-to-noise ratio will be small at large values of k. However, in accordance with the present invention, the signal-to-noise ratio may be increased by using filters to eliminate noise.

In particular, the present invention is directed toward the application of specific mathematical filters and signal processing to obtain clear images of current paths from magnetic field images and electric field images. Filtering and processing the magnetic field images allows images of the currents which produced the electric and magnetic fields to be generated that have better spatial resolution than the spatial resolution of the original electric or magnetic field image. The filters of the present invention are preferably digital filters implemented with software, hardware, or a combination of software and hardware.

The present invention uses known parameters of a circuit from which an electric or magnetic field image was produced to eliminate noise from the electric or magnetic field image. The actual filters used to eliminate the noise will depend upon the specific known parameters. For example, in most integrated circuit designs, the wires usually obey "Manhattan geometry", i.e. all the wires are orthogonal to each other, either running north-south or east-west; or, equivalently, along the plus/minus x-direction or the plus/minus y-direction in the sample plane. The orthogonal relationship of the wires leads to certain features in the Fourier transform of the electric or magnetic field. These features can be used to remove noise from the field image.

Figure 2B:
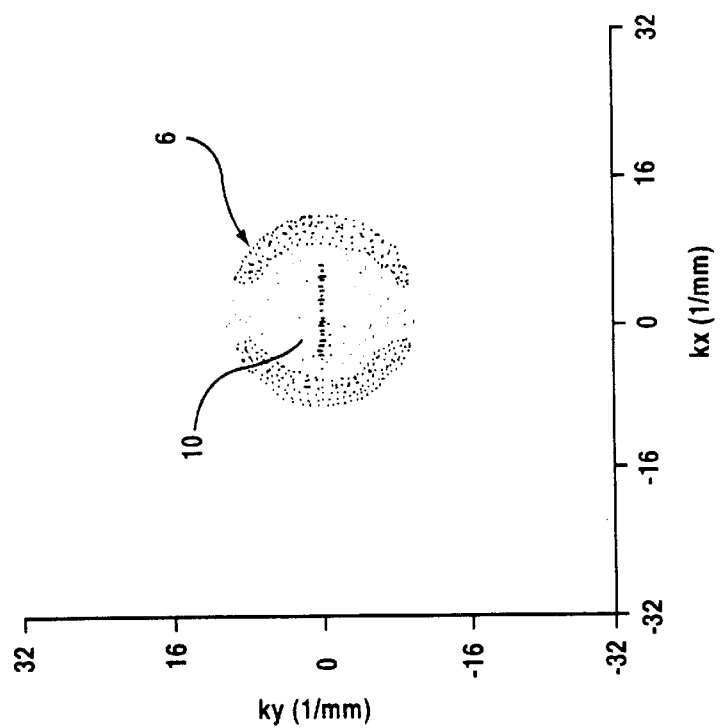
FIGS. 2(a) and 2(b) are graphic representations of the current density data corresponding to the current densities $j_x(k_x, k_y)$ and $j_y(k_x, k_y)$ calculated in Fourier space from the magnetic field of FIG. 1.
Figure 2A:
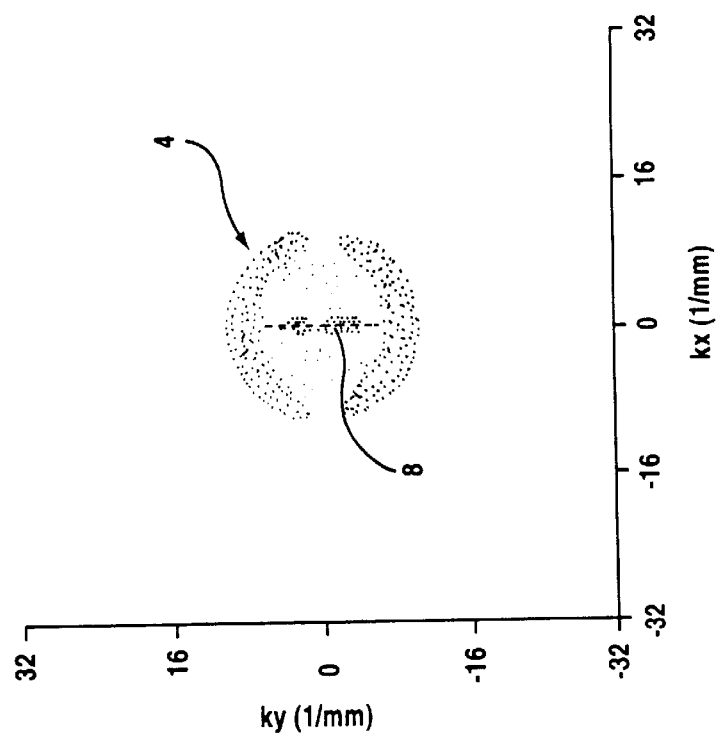

To better illustrate the above discussed approach, a situation will be discussed in a simulated example in which a current is induced to flow in a circuit containing a square loop of wire. The square loop of wire has a Manhattan geometry as discussed above. FIG. 1 shows the normal component of the magnetic fields 2 generated by a 100 $\mu$A current flowing in the square loop of wire at a height of 200 $\mu$m above the plane of the square loop. The strength of the magnetic fields 2 ranges from −31 to 88 nano Tesla. Following the magnetic inversion technique, a Fourier transform is performed on the magnetic field data and the current density $j_x(k_x, k_y)$ and $j_y(k_x, k_y)$ in Fourier space is calculated from equations (3) and (4), respectively. The magnetic field generated by the currents flowing parallel to the x-direction is transformed mostly into the $k_y$-direction, while the magnetic field generated by the currents flowing parallel to the y-direction is transformed mostly into the $k_x$-direction, as shown in FIGS. 2(a) and (b). Because of the orthogonal nature of the square wire loop, the currents are almost entirely flowing in the x and y directions. Therefore, the points in the $k_x$-$k_y$ plane (referred to as $\bar{k}$-space) that are, not on the $k_x$ and $k_y$ axes are mostly noise or undesirable artifacts.

Figure 2C:
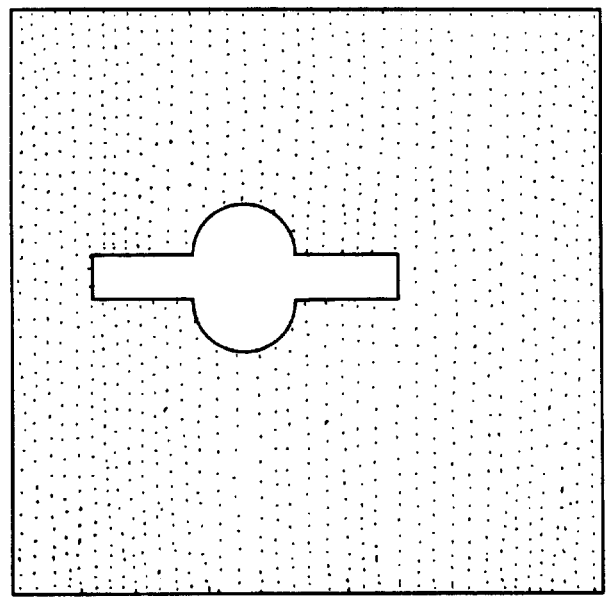
FIGS. 2(c) and 2(d) illustrate keyhole filters in accordance with the graphic representations shown in FIGS. 2(a) and 2(b)
Figure 2D:
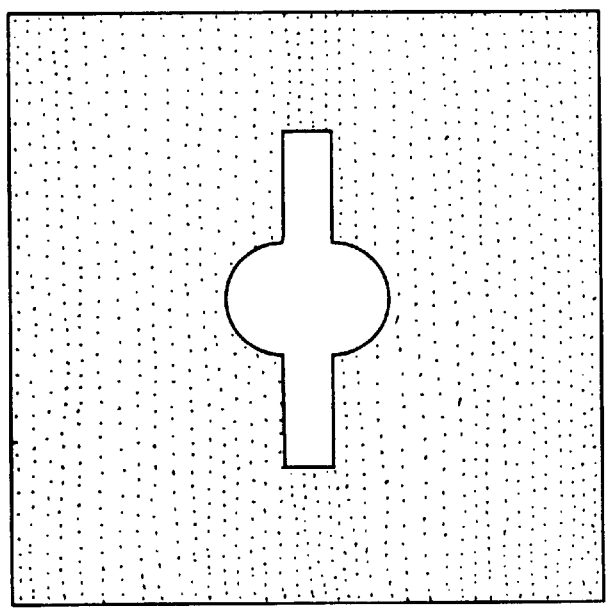
Figure 3B:
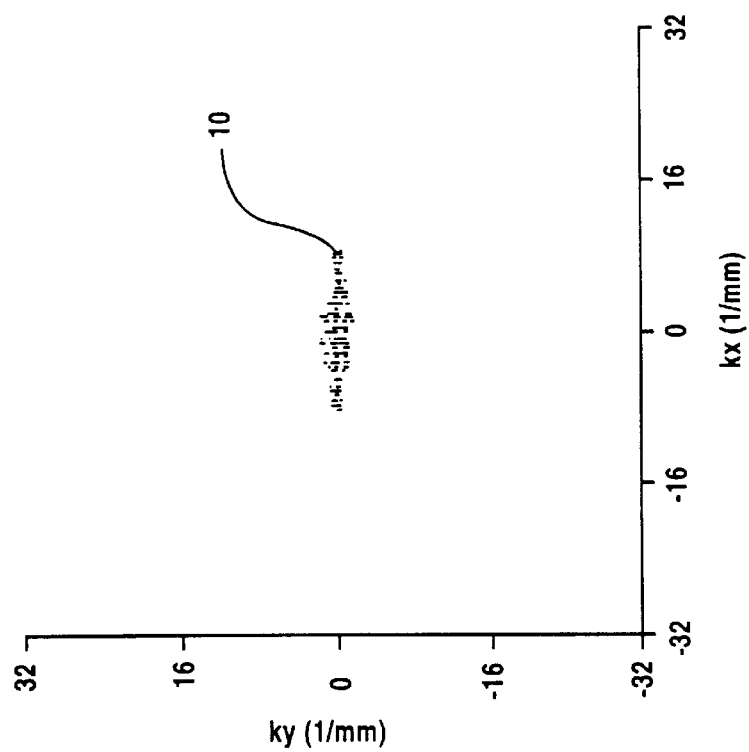
FIGS. 3(a) and 3(b) are graphic representations of the current densities in Fourier space of FIGS. 2(a) and 2(b) after filtering.
Figure 3A:
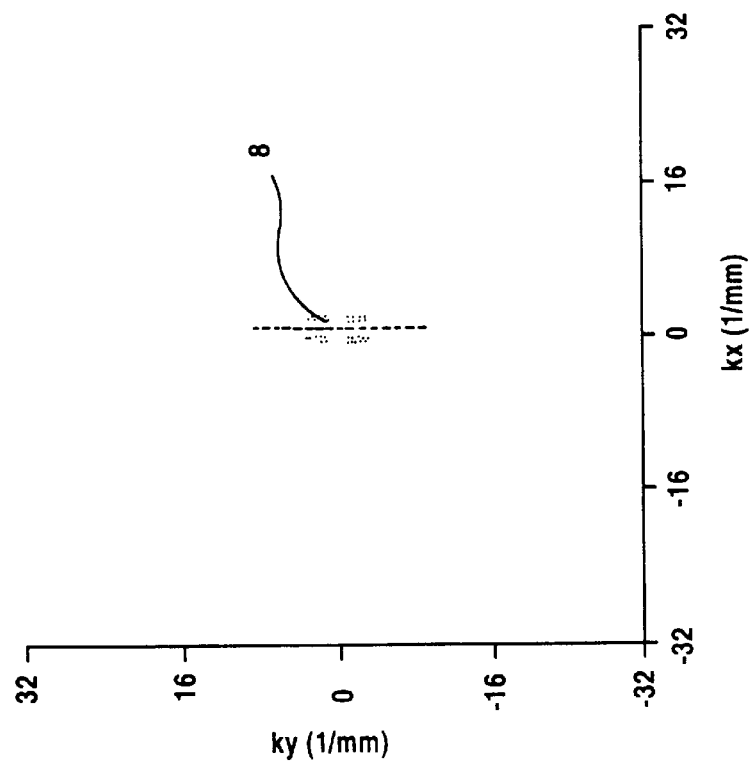

Because it is known that the circuit is orthogonal in nature, most of the noise in the $J_x$ image can be eliminated by applying a filter that retains only the data points 8 in the $k_y$-direction in the Fourier space. In practice, points in a circular region close to the origin are also maintained. This type of filter is referred to as a key-hole "liter because of its shape, as shown in FIG. 2c. By using a keyhole filter all of the noise in the $J_x$ image that is not due to currents flowing in the x-direction can be eliminated (see FIG. 3(a)). Similarly, a keyhole filter such as that shown in FIG. 2d that keeps only the data points 10 in the $k_x$-direction in the Fourier space eliminates noise that is not associated with currents flowing in the y-direction (See FIG. 3(b)). Using a suitable drawing program or drawing software such as ADOBE PHOTOSHOP(™), a suitable filter can be drawn to filter or to eliminate the noise which fall outside of the desired region in Fourier space. A filter is drawn based upon the images in FIGS. 2(a) and 2(b) so that only data points 8 remain in FIG. 3(a) from FIG. 2(a), and so that data points 10 remain in FIG. 3(b) based upon the image in FIG. 2(b). As noted previously, the filter is drawn in the shape of a key-hole, so that appropriate undesirable noise is eliminated. Using image processing software such as TRANSFORM (™) or data processing software such as EXCEL(™), the $J_x(k_x, k_y,)$ and $J_y(k_x, k_y)$ image data are multiplied by the filter to yield the filtered image. For this multiplication process, dark areas of the filter are assigned the value 0 (zero), while white areas are assigned the value 1 (one). The image and filter are then multiplied together, point by point, to produce a filtered image. In this way points at $(k_x, k_y)$ in the original image which correspond to locations $(k_x, k_y)$ which are dark in the filter are removed (set to zero) in the filtered imaged, while points at $(k_x, k_y)$ in the image which correspond to locations $(k_x, k_y,)$ which are white in the filter are unchanged. One could also use more smoother filters, which employ a gray-scale masking (allowing multiplication by values between 1 and zero).

Because the above discussed approach keeps all of the data points in the $k_x$ and $k_y$ directions, the noise along the $k_x$ or $k_y$ directions is not eliminated. However, a cut-off spatial frequency $k_w$ is introduced to eliminate the noise in the $k_x$ or $k_y$ directions at a high spatial frequency. Therefore, it is the value of $k_w$ which ultimately determines the spatial resolution. In other words, the finest features resolvable by this technique in the final image will never be smaller than about $1/k_w$. To construct the final image, after applying the filter in k-space an inverse Fourier transform is performed on the remaining data points. For example, by taking the inverse Fourier transform of the filtered data of FIGS. 3(a) and 3(b), and choosing $k_w$=11 mm$^{-1}$, the current density is obtained in x-y space. FIG. 4 shows the result, plotted as $J_x^2$ and $J_y^2$. The image 12 of FIG. 4 is the desired image of the current paths or wires in the square loop.

There are several advantages to using the filters of the present invention. First, for a given value of $k_w$, the noise in the final image will be much less when the filter is used, than when it is not. Second, for a given electric or magnetic field data set, when the filters are used, larger values of $k_w$ can be used, and thus better spatial resolution can be obtained in the final current image. Third, the filters can also be used to eliminate edge artifacts which arise whenever a Fourier transform is applied to a finite sized data set (this is a result of the well-known Gibb's overshoot phenomena). The idea is that the edges of an image lie along certain directions, and that these directions can be chosen so as not to lie along the same direction as the wires. Application of the filters then will naturally remove the current artifacts associated with the edge. Finally, while the filters of the present invention will work on any circuit with Manhattan geometry, and do not require previous knowledge of the circuits specific wiring layout, they can also be readily adapted by one skilled in the art to a non-Manhattan circuit geometry. In practice, virtually all microelectronic chips and multi-chip modules in use today have restrictions on the wiring geometry. For example, some allow Manhattan geometry plus 45 degree directions. As discussed in more detail below, the filters of the present invention can be adapted to handle such a case.

Filters can also be designed to be chip specific. A chip specific filter would be based upon the known circuit geometry of the specific chip. The filter could then be designed by transforming an image of the wires in the circuit into Fourier space. The Fourier image of the current density points obtained from the magnetic fields data obtained from the chip would then be filtered to remove all of the current density points which do not represent current flowing along one of the known current paths, using a filter based on the transformed wire image. Therefore, by knowing the specific circuit wiring layout, filters can be designed to eliminate current density data points which do not represent current flowing along a wire path of the circuit. Current density points which do not represent current flowing down a circuit current path are almost entirely due to noise and edge effects. By designing a chip specific filter, a high degree of resolution can be obtained in the final image. As can be seen from the above discussion, the complexity of a chip specific filter will depend upon the complexity of the specific chip.

Figure 5:
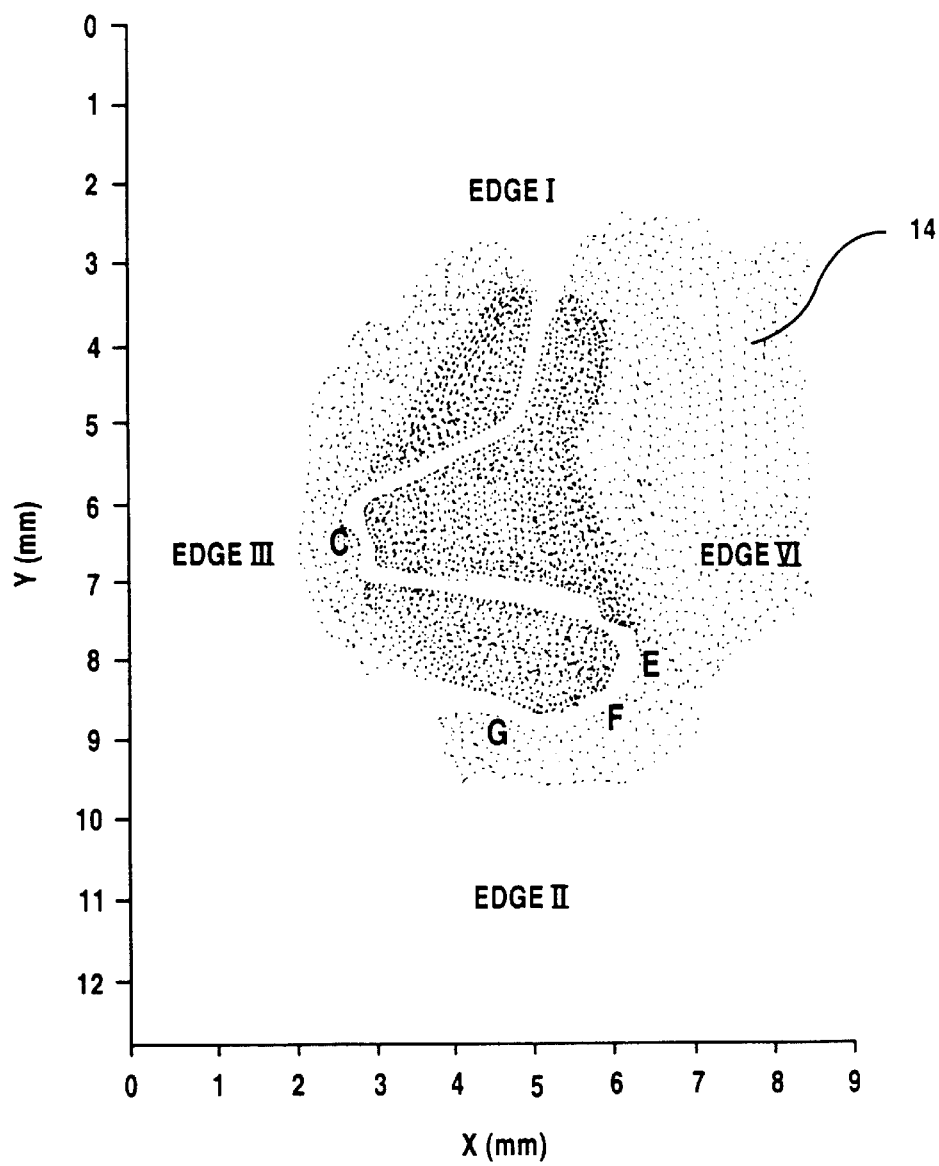
FIG. 5 is a magnetic field image from an integrated circuit.

As a further illustration of the applicability of the present invention, a scanning SQUID microscope was utilized to image the magnetic fields above a multi-chip module which was known to have a non-Manhattan geometry. In this case, the geometer was Manhattan plus the 45° directions. A current of about 86 mA was applied to two wires in the sample circuit and the sample circuit was raster scanned under the SQUID at a separation of about 340 microns. The normal component of magnetic field image 14 from the sample, as detected by the SQUID, is shown in FIG. 5. The sampling interval is 18 $\mu$m and 25 $\mu$m in the X and Y directions, respectively. The maximum amplitude of the magnetic field is approximately 50 nT.

Figure 6A:
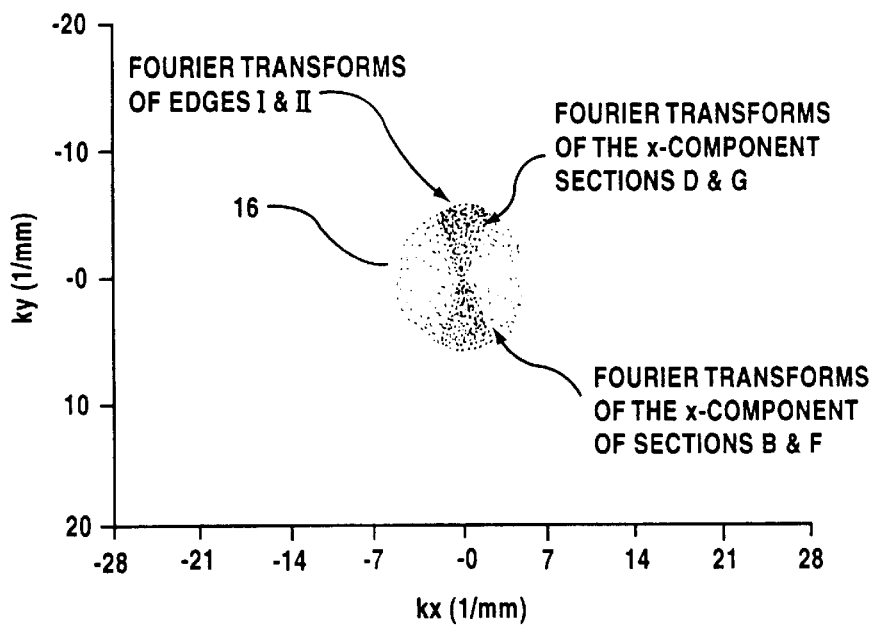
FIGS. 6(a) and 6(b) graphically show the current density images $j_x(k_x, k_y)$ and $j_y(k_x, k_y)$ calculated in Fourier space from the magnetic field of FIG. 5.
Figure 6B:
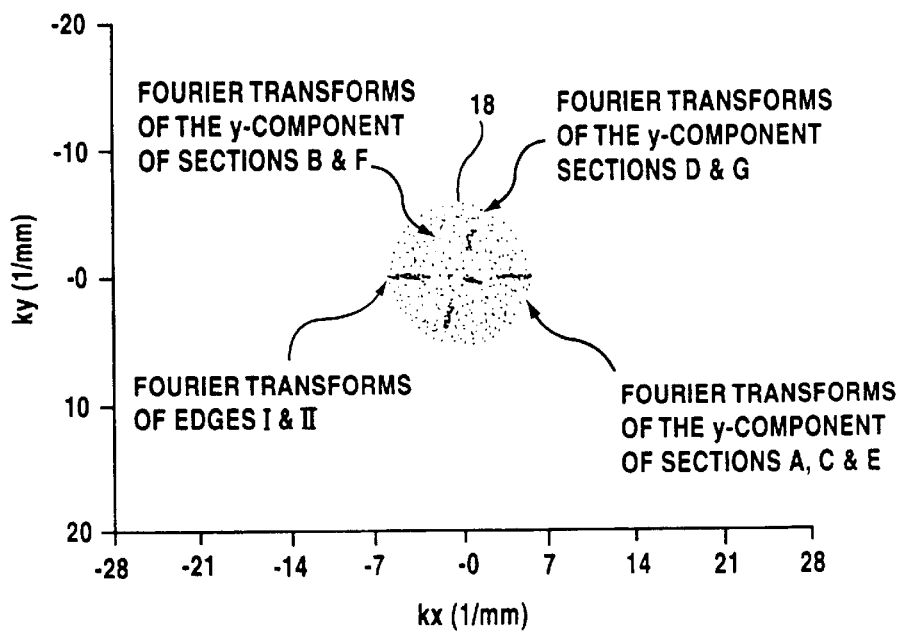
Figure 7:
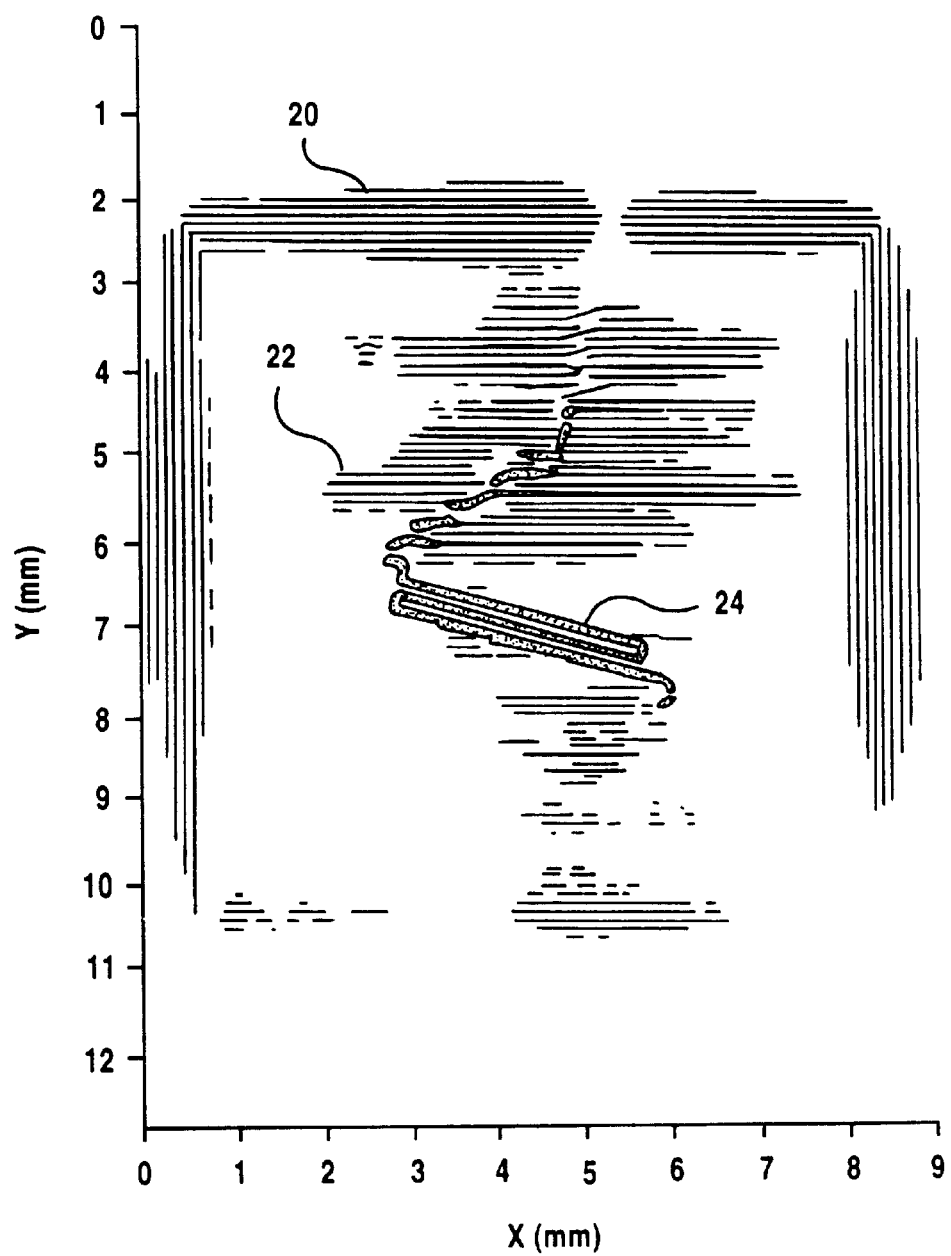
FIG. 7 is an image of $J_x^2(x, y) + J_y^2(x, y)$ obtained from inverse Fourier transforms of the data in FIGS. 6(a) and 6(b)
Figure 8A:
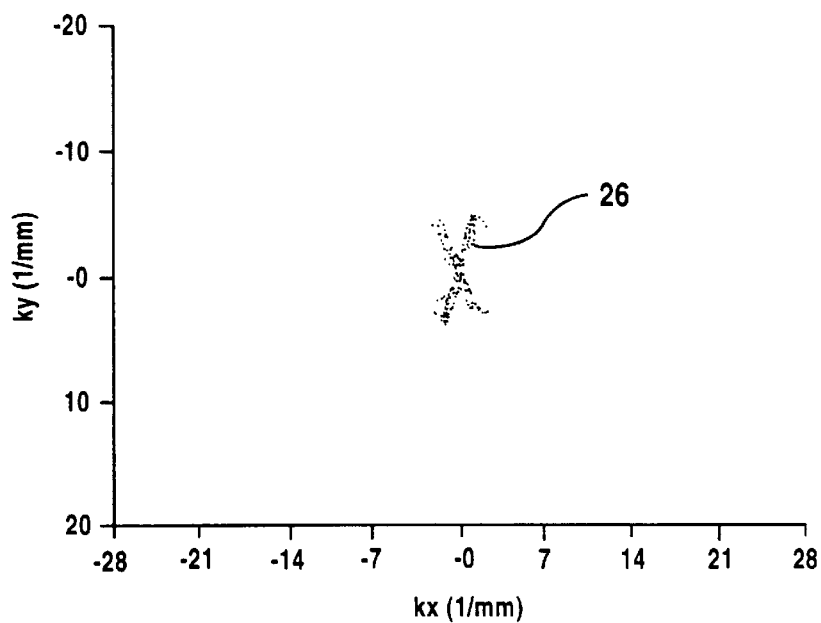
FIGS. 8(a) and 8(b) graphically show the current density images $j_x(k_x, k_y)$ and $j_y(k_x, k_y)$ calculated in Fourier space from the magnetic field of FIG. 5 after filtering out the edges and noise.
Figure 8B:
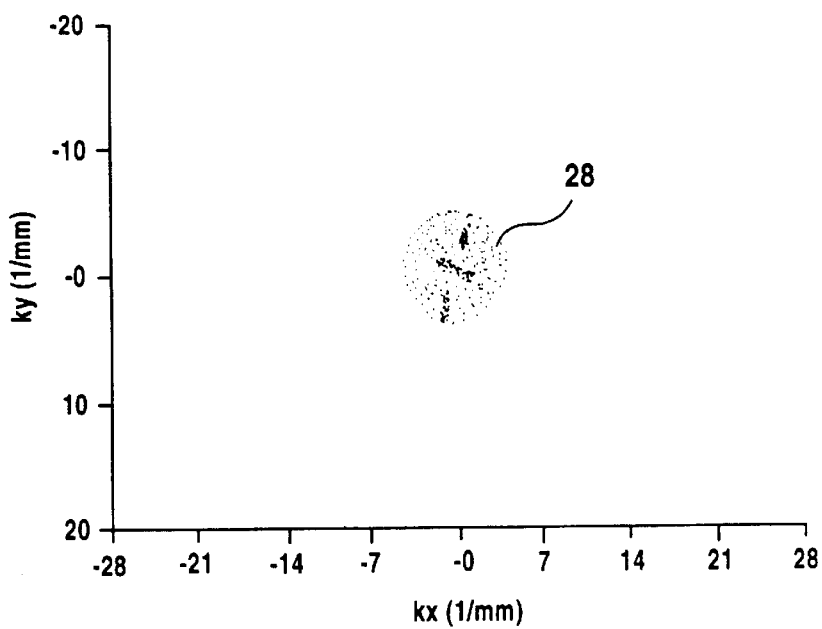
Figure 9:
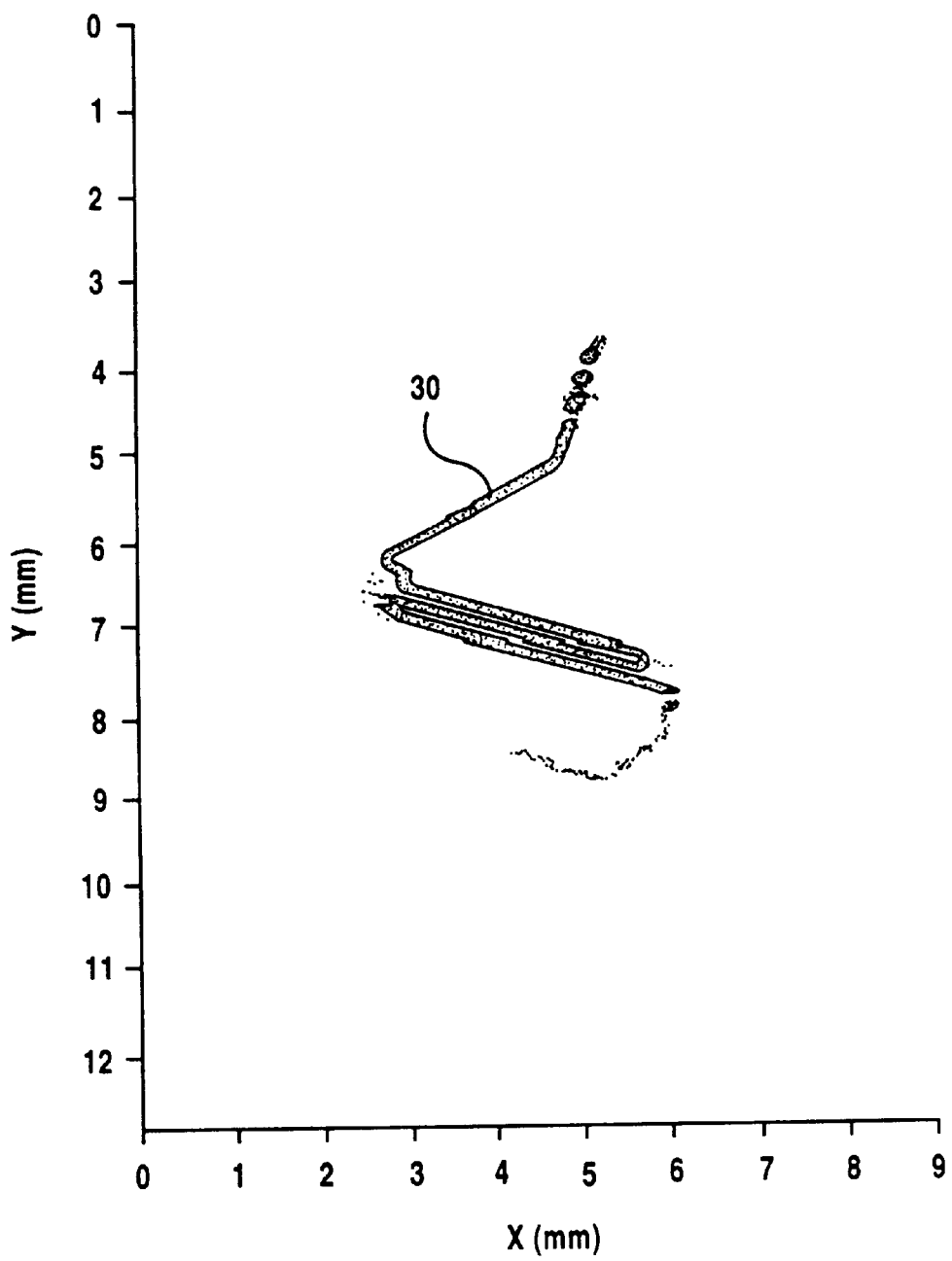
FIG. 9 is an image of $J_x^2(x, y) + J_y^2(x, y)$ obtained from inverse Fourier transforms of the data in FIGS. 8(a) and 8(b)
Figure 11:
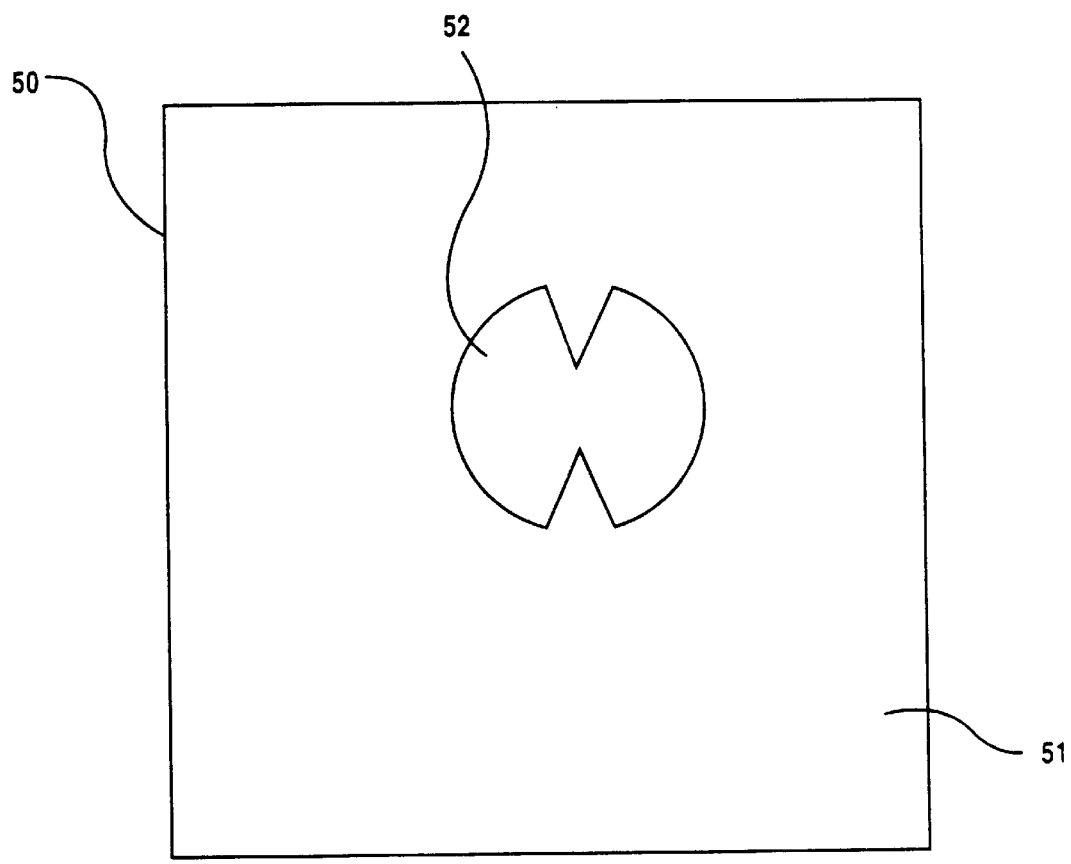
FIG. 11 illustrates a filter for the image shown in FIG. 6(a).

Next, a Fourier transform was performed on the magnetic field data 14. From equations (3) and (4), the current densities $j_y(k_x, k_y)$ 16 and $j_y(k_x, k_y)$ 18 were then calculated as shown in FIGS. 6(a) and 6(b). If an inverse Fourier transform of the data shown in FIGS. 6(a) and 6(b) is taken, the resulting $J^2(x, y)$ in x-y space includes noise and ripples 20 (artifacts) from the edges, as shown in FIG. 7. It should be noted that, in FIG. 7, the undesirable streaks 22 from the edges propagate through the image and distort the actual current paths 24. By applying the appropriate filters on the data in FIGS. 6(a) and (b), we can eliminate the edge artifacts 20 and the noise that is not along the same directions as the currents 24. FIGS. 8(a) and (b) show $j_y(k_x, k_y)$ 26 and $j_y(k_x, k_y)$ 28 after using selective filters to remove the edge artifacts and noise, using $k_w$=6 mm$^{-1}$. FIG. 9 shows the inverse Fourier transform 30 obtained from FIGS. 8(a) and (b). The square amplitude of the current density is plotted in x-y space. It should be noted that the selective filtering performed on the data in FIGS. 6(a) and (b) significantly reduced or eliminated the edge artifacts and noise, producing a markedly clearer image of the current paths. Appropriate filters for the magnetic field image in FIG. 5 are drawn based upon the Fourier transformed images shown in FIG. 6. Appropriate filters are drawn to eliminate edge artifacts and noise, with a selected $k_w$ of 6 mm$^{-1}$. In Fourier space, therefore, it can be seen that the current density illustrated in FIG. 8 contains much less noise than that which is illustrated in FIG. 6. Performing an inverse Fourier transform on the filtered images of FIG. 8 results in the much-improved image 30 of FIG. 9. FIG. 11 illustrates filter 50 which is drawn for filtering the image shown in FIG. 6(a) in order to yield the filtered image shown in FIG. 8(a). Using an appropriate graphic program such as ADOBE PHOTOSHOP(™), filter 50 includes masking portion 51, and "pass-through" portion 52. Masking portion 51 is drawn so as to eliminate the Fourier transforms of edges I and II, so as to provide the more defined current density shown in FIG. 8(a). A similar filter is provided for the current density illustrated in FIG. 6(b), to yield the filtered image shown in FIG. 8(b).

In order to more clearly discuss how equations (3) and (4) can be obtained, and therefore calculate the $J_x$ and the $j_y$ components, the following are macrofunctions scripts for the conversions, utilizing the "TRANSFORM(™)" software:

code line 1 TransferFN=8.3e−6: Transfer function for converting voltage to magnetic field.

code line 2 Gain=100: Gain of the amplifier used in data acquisition.

code line 3 B=((R23S21inv/Gain)*TransferFN): Converting Volt to magnetic field unit (Tesla). R23S21inv is the raw data file.

code line 4 B_c=complex(B, O*B): Construct a complex matrix of magnetic field which the real part is from line 3 and the imaginary part is zero.

code line 5 B_fft=fft(B_c, 1): Take Fast Fourier Transform (FFT) of the complex magnetic field. The 1 is the argument of fft refers to a forward transform.

code line 6 B_fft_re=real(B_fft): Extract the real part of the Fourier transformed magnetic field.

code line 7 B_fft_im=imag(B_fft): Extract the imaginary part of the Fourier transformed magnetic field.

code line 8 kx=c(B_fft_re): Construct the $k_x$ matrix.

code line 9 ky=r(B_fft_re): Construct the $k_y$ matrix.

code line 10 k=sqrt(ky2+kx2): Construct the k matrix.

code line 11 kx_red=zapnan(kx/k, 1): Construct the reduced-$k_x$ matrix; the ratio of $k_x$ and k in Eq. (3).

code line 12 ky_red=zapnan(ky/k, 1): Construct the reduced-$k_y$ matrix; the ratio of $k_x$ and k in Eq. (4).

code line 13 z=0.340: z is the input parameter which is the SQUID-to-sample separation. In this case, the sample is the wire that produces magnetic field. The unit of z we use in this notebook is millimeter (mm).

code line 14 d=0.010: d is another input parameter which is the thickness of the wire, also in the unit of mm.

code line 15 pi=a cos(−1): Define a numerical value of $\pi$.

code line 16 mu=4*pi*1e−10: mu is the permeability of free space, which equals to $4\pi \times 10^{-7}$ in SI unit. But in this notebook, we use mu=$4\pi \times 10^{-10}$ because we use mm unit.

code line 17 flt=(2/(mu*d))*exp(2*pi*k*z): Construct an exponential factor matrix in Eq. (3) & (4).

code line 18 filter=zapnan (zapnan((1/flt)*flt,0)*flt,0): The exponential term in line 17 can be too large for "Transform" to handle. "Transform" will assign string "Inf" (meanings infinity) to a very large value which causes errors in later steps. The purpose of this line is to eliminate the string "Inf" and set it to zero however, this happens at a very large value of k, larger than the value of k we ever need.

code line 19 kw=6: kw is the maximum value of k we will use to make a window to eliminate noise due to the exponential growth term in line 17. In other words, kw is the cut-off spatial frequency mentioned in the statement of invention. The larger kw, the finer feature we can get at the end of the process. The unit kw is mm$^{-1}$.

code line 20 knew=LEmask(k,kw)*k: Construct a new matrix of k with non-zero value within the radius kw. In other words, LEmask(kx,kw) function is a logic function that assigns unity to the elements of the k-matrix whose values are less than or equal to kw, otherwise zero. We then multiply with k to restore the original k value within kw radius.

code line 21 window=LTmask(0.5*(1+cos(pi*knew/kw)), 1)*0.5*(1+cos(pi*knew/kw)): Line 21 defines a "Hanning" window that we use to eliminate high spatial frequency components. Hanning window is a weighting function that gives less weight at high k value.

code line 22 Bfft_filter_win_re=Bfft_re*filter*window: Multiply lines 6, 18 and 21 together.

code line 23 Bfft_filter_win_im=B_fft_im*filter*window: Multiply lines 7, 18 and 21 together.

code line 24 jx_all=complex(Bfft_filter_win_im*ky_ed, -1*(Bfft_filter_win_re)*ky_red): In line 24, we calculate $j_x(k_x,k_y)$ according to Eq. (3).

code line 25 jx_all_flt=jx_all*(jxflt1_TIF/255): Multiply the result of line 24 with the "mahattanized" filter for $j_x(k_x,k_y)$. In this notebook, the "mahattanized" filter filename is jxflt1_TIF/255, which is 0 and 1 matrix. The zero elements in the "mahattanized" filter are used to eliminate undesired data in the $j_x(k_x,k_y)$ matrix. (See the image of jxflt1_TIF below). The filter file has to be opened by "Transform" before executing this line.

code line 26 jx=real(ff(jx_all_flt-1)): Taking the real part of the inverse FFT of jx_all_flt from line 25 yields $J_x(x,y)$. The -1 in the argument of fft refers to an inverse transform.

code line 27 jy_all=complex(-1*(Bfft_filter_win_im)*kx_red, Bfft_filter_win_re*kx_red): In line 27, we calculate $j_y(k_x,k_y)$ according to Eq. (4).

code line 28 jy_all_fit=jy_all*(jyflt1_TIF/255): Multiply the result of line 27 with the "mahattanized" filter for $j_y(k_x,k_y)$. In this notebook, the "mahattanized" filter filename is jyflt1_TIF/255, which is 0 and 1 matrix. The zero elements in the "mahattanized" filter are used to eliminate undesired data in the $j_y(k_x,k_y)$ matrix. (See the image of jyflt_TIF below). The filter file has to be opened by Transform" before executing this line.

code line 29 jy=real(fft(jy_all_flt, -1)): Taking the real part of the inverse FFT of jy_all_flt from line 25 yields $J_y(x,y)$. The -1 in the argument of fft refers to an inverse transform.

code line 30 jsqr=jx*2+jy*2: Calculating the current density squared, $J^2(x,y)=J_x^2(x,y)+J_y^2(x,y)$.

Although the above-discussed embodiment utilizes the Fast Fourier transform (FFT) and inverse Fast Fourier transform, it is possible to use other mathematical transforms such as Fourier transforms, Laplace transforms, Hankel transforms, etc. In accordance with the invention, when a transform is used to convert the magnetic field data into current density data, the inverse of the transform is used to convert the filtered data back into image data. It is conceivable, of course, that the magnetic field data could be converted to current density data using an inverse Fourier transform, and then convert it back to image data using a forward Fourier transform. In such a case, "inverse" is considered a relative term.

Figure 10:
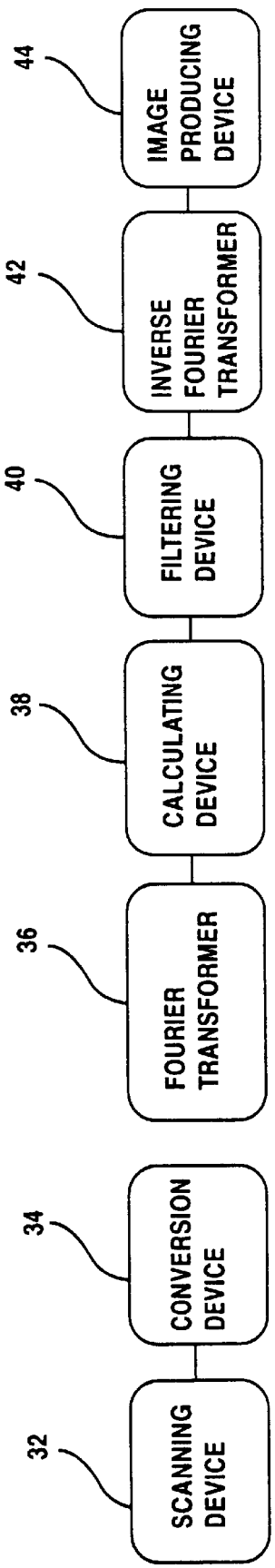
FIG. 10 is a block diagram of an apparatus in accordance with the present invention.

FIG. 10 depicts a block diagram of an apparatus for imaging current flow in an electronic circuit, including microelectronic circuits and integrated circuits, in accordance with an embodiment of the present invention. The apparatus includes a scanning device 32 for scanning an electronic circuit to produce a set of data related to the strength of the magnetic or electric fields produced by the electronic circuit at a distance above the electronic circuit. Preferably, the data set includes an array of voltage values, which are directly proportional to the normal component of magnetic field produced by the electronic circuit at a position above the circuit, and x-y coordinates corresponding to the position of the scanning device 32 when the corresponding voltage values were sensed. Alternatively, the sensor could detect another component, such as the x-component or the y-component, or components of the magnetic field. Additionally, the scanning device can produce values which are directly proportional to the electric fields produced by the electronic circuit, or to the electromagnetic field such as optical, infrared, or microwave power produced by the circuit.

A converting device 34 receives the array of voltage values and converts the voltage values to an array of magnetic field values. The converted values are then sent to a Fourier transformer 36 which performs a Fourier transform on the array of magnetic field values to obtain an array of transformed magnetic field values. A calculating device 38 then calculates the current density in Fourier space from the array of transformed magnetic field values by performing a magnetic inversion technique as discussed above. The current density values in Fourier space produced by the calculating device 38 include a $k_x$ and a $k_y$ image. Alternatively, the electric field values can be converted to values representing the Fourier transform of the spatial distribution of charge in the electronic circuit. The current density values are then received by a filtering device 40 which removes certain data from the current density values based upon known parameters of the electronic circuit. The filtering function of the filtering device 40 can be best understood by reference to the $k_x$ and $k_y$ images. For example, if it is known that the wires in an electronic circuit has an orthogonal circuit geometry, the filtering device will preferably remove values not lying near the y-axis in the $k_x$ image and values not lying along the x-axis in the $k_y$ image. In addition, the filtering device 40 will maintain current density data points in the $k_x$ and $k_y$ space images that have a cutoff frequency below a certain value. Thus, the filtering device 40 maintains data points in a keyhole shaped region in the $k_x$ and $k_y$ images. The data points remaining after filtering are then sent to an inverse Fourier transformer 42 which performs an inverse Fourier transform on the data points to obtain current density values in x-y space. The current density data points in x-y space are received by an image producing device 44 which plots the current density values in x-y space in order to produce an image of currents flowing in the electronic circuit. Alternatively, if the sensor were used to detect voltage from a circuit, the output of the Fourier transformer 42 would be an image showing the spatial distribution of electric charge or voltage levels in the wires of the circuit.

Although the present invention has been fully described in connection with the preferred embodiment thereof with reference to the accompanying drawings, it should be noted that various changes and modifications will be apparent to those skilled in the art. Such changes and modifications are to be understood as included within the scope of the present invention as defined by the appended claims.

We claim:

1. A method of imaging microelectronic circuits, said method comprising:

providing a scanning device for scanning magnetic fields generated by microelectronic circuits;

scanning a microelectronic circuit with said scanning device wherein said scanning device generates magnetic field data corresponding to scanned magnetic fields;

performing a mathematical transform of said magnetic field data to yield current density data;

filtering the current density data to generate filtered data, said filtered data containing data points in one direction and isolating current flow in a flow direction;

performing an inverse mathematical transform of said filtered data, thereby yielding final filtered image data; and creating a final image based upon said final filtered image data.

2. The method as recited in claim 1, wherein said filtering isolates current flow by maintaining the data points in the one direction and also maintaining data points in a circular region close to an origin of the current density data.

3. The method as recited in claim 1, wherein said filtering includes filtering frequencies above a cut-off spatial frequency kW.

4. The method as recited in claim 1, wherein said measuring magnetic fields includes measuring magnetic fields of current paths which are orthogonal to each other.

5. The method as recited in claim 1, wherein said filtering includes removing current density data points representing current flowing in a direction which is not parallel to the current paths.

6. The method of claim 1 wherein the current density data is filtered by removing current density data points representing current flowing in a direction that does not correspond to a possible current path in the electronic circuit.

7. The method of claim 1 wherein performing the mathematical transform comprises performing a Fourier transform on the magnetic field data to obtain current density data comprising a $j_x$-image and a $j_y$-image in Fourier space.

8. The method of claim 7 wherein filtering the current density data comprises:

calculating the magnetic field data in a $k_x$-$k_y$ plane such that substantially all of the current paths in the electronic circuit are along a $k_x$-axis or a $k_y$-axis;

calculating a $j_x$-image and a $j_y$-image of the current density data in Fourier space in the $k_x$-$k_y$ plane such that current density data points lying along the $k_x$-axis of the $j_y$-image represent currents flowing in the y-direction and current density data points lying along the $k_y$-axis of the $j_x$-image represent currents flowing in the x-direction; and filtering the current density data by removing current density data points that do not lie substantially on the $k_x$-axis of the $j_y$-image or the $k_y$-axis of the $j_x$-image.

9. The method of claim 8 further comprising eliminating edge artifacts which arise in the current density data images in Fourier space whenever a Fourier transform is applied to a finite sized data set by choosing a direction in which the edge artifacts in the current density data images lie so that the edge artifacts do not lie in a same direction as the current paths.

10. An apparatus for producing an image of currents flowing in an electronic circuit, the apparatus comprising:

a magnetic field measuring device for producing an image spatially representing a magnetic field produced at a distance above the electronic circuit by currents flowing in the electronic circuit;

calculating means for calculating a current density image from the image representing the magnetic field produced by currents flowing in the circuit;

filtering means for filtering a mathematical transform of the current density image based upon restrictions placed upon a wiring geometry of the electronic circuit, thereby providing filtered data; and an image producing device for producing an image of the currents flowing in the electronic circuit from the filtered data.

11. The apparatus of claim 10, wherein said filtering means filters a Fourier transform of the current density image.

12. The apparatus of claim 11, wherein the calculating means further comprises magnetic inversion means for calculating the current density image in Fourier space using a magnetic inversion technique.

13. The apparatus of claim 10 wherein the magnetic field measuring device comprise a scanning superconducting quantum interference device microscope.

14. The apparatus of claim 10, wherein the magnetic field comprises magnetic field data in a $k_x$-$k_y$ plane axis such that substantially all of the current paths in the electronic circuit are along a $k_x$-axis or a $k_y$ axis, and wherein the calculating means calculates a $j_x$-image and a $j_y$-image of the current density data such that current density data points lying along the $k_x$-axis of the $j_y$-image represent the mathematical transform of currents flowing in the y-direction and current density data points lying along the $k_y$-axis of the $j_x$-image represent the mathematical transform of currents flowing in the x-direction, and wherein the filtering means filters the current density data by removing current density data points which do not lie substantially on the $k_x$-axis of the $j_y$-image the $k_y$-axis of the $j_x$-image.

15. A method of creating an image of currents flowing through current paths in an electronic circuit, said method comprising:

providing a magnetic field measuring device for measuring magnetic fields at a distance above an electronic circuit;

providing a computing device including a display and image processing means for producing and manipulating image data;

scanning the electronic circuit with the magnetic field measuring device to produce magnetic field data corresponding to an image representing the magnetic field above the electronic circuit based upon the currents flowing in the electronic circuit;

performing a mathematical transform of said magnetic field data to yield current density data;

displaying the current density data as an image on the display;

providing a filter corresponding to the image, whereby said filter is prepared with the image processing means of the computing device, said filter being of a shape selected to eliminate undesirable data points of the image based upon the current density data, by leaving desirable data points along certain directions and eliminating the undesirable data points in other directions;

multiplying image data corresponding to the filter with the current density data, thereby yielding filtered data;

performing an inverse transform on said filtered data; and displaying a filtered image corresponding to the filtered data.

16. A method as recited in claim 15, wherein said step of performing a mathematical transform on said magnetic field data includes performing a Fourier transform or Fast Fourier Transform thereupon.

17. A method as recited in claim 15, wherein said step of providing a magnetic field measuring device comprises providing a superconducting quantum interference device microscope.

18. The method of claim 15, wherein said step of performing a mathematical transform of said magnetic field data comprises a step of calculating the magnetic field data in a $k_x$-$k_y$ plane such that substantially all of the current paths in the electronic circuit are along a $k_x$-axis or a $k_y$-axis, and wherein a $j_x$-image and a $j_y$-image of the current density data in the $k_x$-$k_y$ plane are calculated such that current density data points lying along the $k_x$-axis of the $j_y$-image represent currents flowing in the y-direction and current density data points lying along the $k_y$-axis of the $j_x$-image represent currents flowing in the x-direction, and wherein the current density data is filtered in the multiplication step by removing current density data points that do not lie substantially on the $k_x$-axis of the $j_y$-image or the $k_y$-axis of the $j_x$-image.

19. A method as recited in claim 15, wherein said step of providing a magnetic field measuring device comprises providing a Hall effect sensor.

20. A method as recited in claim 15, wherein said step of providing a magnetic field measuring device comprises providing a magnetoresistive sensor.

21. A method as recited in claim 15, wherein said step of providing a magnetic field measuring device comprises providing a flux-gate magnetometer transistor microscope.

22. A method of imaging microelectronic circuits, said method comprising:

providing a scanning device for scanning electric fields generated by microelectronic circuits;

scanning a microelectronic circuit with said scanning device wherein said scanning device generates electric field data corresponding to scanned electric fields;

performing a mathematical transform of said electric field data to yield charge distribution data:

filtering the charge distribution data to generate filtered data, said filtered data containing data points in one direction, thereby isolating charge distribution;

performing an inverse mathematical transform of said filtered data, thereby yielding final filtered image data; and creating a final image based upon said final filtered image data.

23. A method as recited in claim 22, wherein said charge distribution data comprises voltage level data.

24. A method as recited in claim 22, wherein said filtering isolates change density by maintaining the data points in the one direction and also maintaining data points in a circular region close an origin of the charge distribution data.

25. A method as recited in claim 22, wherein said filtering includes a step of filtering frequencies above a cut-off spatial frequency $k_w$.

26. A method as recited in claim 22, wherein said measuring of electric fields includes measuring electric fields of wires which are orthogonal to each other.

27. The method as recited in claim 22, wherein said filtering includes removing charge distribution data points in directions which are not parallel to the wires.

28. The method of claim 22 wherein the charge distribution data is filtered by removing charge distribution data points in directions which do not correspond to a possible wire in the electronic circuit.

29. The method of claim 22 wherein performing the mathematical transform comprises performing a Fourier transform on the electric field data to obtain charge distribution data comprising a $j_x$-image and a $j_y$-image in Fourier space.

30. The method of claim 29 wherein filtering the charge distribution data comprises:

calculating the electric field data in a $k_x$-$k_y$ plane such that substantially all of the wires in the electronic circuit are orthogonal to a $k_x$-axis and a $k_y$-axis;

calculating an image of the charge distribution data in Fourier space in the $k_x$-$k_y$ axis such that charge distribution data are on the $k_x$-axis or $k_y$-axis, representing voltage on wires running along a y-axis or an x-axis; and filtering the charge distribution data by removing charge distribution data points that do not lie substantially on the $k_x$-axis or the $k_y$-axis.

31. The method of claim 30 further comprising eliminating edge artifacts which arise in the charge distribution data images in Fourier space whenever a Fourier transform is applied to a finite sized data set by choosing a direction in which the edge artifacts in the charge distribution data images lie so that the edge artifacts do not lie in a same direction as the wires.

32. An apparatus for producing an image of currents flowing in an electronic circuit, the apparatus comprising:

an electric field measuring device for producing an image spatially representing a electric field produced at a distance above the electronic circuit by voltages in the electronic circuit;

calculating means for calculating a charge distribution image from the image representing the electric field produced by currents flowing in the circuit;

filtering means for filtering a mathematical transform of the charge distribution image based upon restrictions placed upon a wiring geometry of the electronic circuit, thereby providing filtered data; and an image producing device for producing an image of one of voltage levels and charge distribution in the electronic circuit from the filtered data.

33. The apparatus of claim 32, wherein said filtering means filters a Fourier transform or Fast Fourier transform of the charge distribution image.

34. The apparatus of claim 33, wherein the calculating means further comprises an inversion means for calculating the charge distribution image in Fourier space using an inversion technique.

35. The apparatus of claim 32 wherein the electric field measuring device comprise a scanning single electron transistor.

36. The apparatus of claim 32, wherein the electric field comprises electric field data in a $k_x$-$k_y$ plane such that substantially all of the wires in the electronic circuit are parallel to a $k_x$-axis or a $k_y$-axis, and wherein the calculating means calculates an image of the charge distribution data such that charge distribution data points lying along the $k_x$-axis represents wires running along the y-direction and charge distribution data points lying along the $k_y$-axis of the image represent the mathematical transform of wires running in the x-direction, and wherein the filtering means filters the charge distribution data by removing charge distribution data points which do not lie substantially on the $k_x$-axis of the image or the $k_x$-axis of the image.

37. A method of creating an image of voltage levels on wires in an electronic circuit said method comprising:

provifing an electric field measuring device for measuring electric fields at a distance above an electronic circuit;

providing a computing device including a display and image processing means for producing and manipulating image data;

scanning the electric circuit with the electric field measuring device to produce electric field data corresponding to an image representing the electric field above the electronic circuit based upon the voltage levels in the electronic circuit;

performing a mathematical transform of said electric field data to yield charge distribution data;

displaying the charge distribution data as an image on the display;

providing a filter corresponding to the image, whereby said filter is prepared with the image processing means of the computing device, said filter being of a shape selected to eliminate undesirable data points of the image based upon the charge distribution data;

multiplying image data corresponding to the filter with the charge distribution data, thereby yielding filtered data;

performing an inverse transform on said filtered data; and displaying a filtered image corresponding to the filtered data.

38. A method as recited in claim 37, wherein performing the mathematical transform on said electric field data includes performing a Fourier transform thereupon.

39. A method as recited in claim 37, wherein providing the electric field measuring device comprises providing a scanning single electron transistor.

40. The method of claim 37, wherein performing the mathematical transform of said electric field data comprises a step of calculating the electric field data in a $k_x$-$k_y$ plane such that substantially all of the wires in the electronic circuit are orthogonal to a $k_x$-axis and a $k_y$-axis, and wherein the charge distribution data in the $k_x$-$k_y$ plane are calculated such that charge distribution data points lying along the $k_x$-axis of the image represent wires running in the y-direction and charge distribution data points lying along the $k_y$-axis of the image represent wires running in the x-direction, and wherein the charge distribution data is filtered in the multiplication step by removing charge distribution data points that do not lie substantially on the $k_x$-axis of the image or the $k_y$-axis of the image.

41. A method as recited in claim 32, wherein providing the electric field measuring device comprises providing a single electron transistor microscope.

* * * * *